United States Patent
Gleich

(10) Patent No.: US 8,874,188 B2
(45) Date of Patent: Oct. 28, 2014

(54) ARRANGEMENT AND METHOD FOR INFLUENCING AND/OR DETECTING MAGNETIC PARTICLES

(75) Inventor: Bernhard Gleich, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 247 days.

(21) Appl. No.: 13/139,380

(22) PCT Filed: Dec. 10, 2009

(86) PCT No.: PCT/IB2009/055645
§ 371 (c)(1),
(2), (4) Date: Jun. 13, 2011

(87) PCT Pub. No.: WO2010/070547
PCT Pub. Date: Jun. 24, 2010

(65) Prior Publication Data
US 2011/0241663 A1    Oct. 6, 2011

(30) Foreign Application Priority Data

Dec. 17, 2008  (EP) ..................................... 08171979

(51) Int. Cl.
*A61B 5/05*   (2006.01)
*G01R 33/12*  (2006.01)
*G01N 27/72*  (2006.01)
*H03F 3/00*   (2006.01)

(52) U.S. Cl.
CPC  *A61B 5/05* (2013.01); *H03F 3/005* (2013.01); *A61B 5/0515* (2013.01)
USPC .......................................... 600/409; 328/228

(58) Field of Classification Search
USPC .......... 600/407–409, 420, 422–425; 324/204, 324/228, 307, 318; 607/105; 73/53.01; 702/57; 328/204, 228, 307, 309, 318; 307/104–105, 401; 363/39–44
See application file for complete search history.

(56) References Cited

U.S. PATENT DOCUMENTS

2006/0033499 A1*  2/2006  Flexman et al. .............. 324/322
2007/0194895 A1   8/2007  Apostolopoulos
2008/0143459 A1*  6/2008  Vernickel et al. ........... 333/24 C
2008/0204009 A1*  8/2008  Gleich et al. ................. 324/228

FOREIGN PATENT DOCUMENTS

DE   10151778 A1   10/2001
WO   8504258      9/1985
WO   9803887      1/1998

(Continued)

OTHER PUBLICATIONS

By B. Gleich et al, "Tomographic Imaging Using the Nonlinear Response of Magnetic Particles", Nature Publishing Group, Letters, Philips Research, Hamburg, Germany, 2005, pp. 1214-1217.

*Primary Examiner* — Long V. Le
*Assistant Examiner* — Lawrence Laryea

(57) ABSTRACT

An arrangement and a corresponding method for influencing and/or detecting magnetic particles in a region of action include storing required reactive energy in a tank circuit, which is preferably operating at the center frequency of a magnetic particle imaging (MPI) drive field. Reactive elements, such as capacitors and/or inductors, couple one or more tank circuits to the drive field resonator. The coupling strength maybe varied by switching additional reactive elements into and out of the coupling unit to vary the strength of coupling.

10 Claims, 6 Drawing Sheets

(56) References Cited

FOREIGN PATENT DOCUMENTS

| | | | |
|---|---|---|---|
| WO | 2006035359 | A2 | 4/2006 |
| WO | 2008078244 | A2 | 7/2008 |
| WO | 2010008478 | A2 | 1/2010 |

\* cited by examiner

ARRANGEMENT AND METHOD FOR INFLUENCING AND/OR DETECTING MAGNETIC PARTICLES

FIELD OF THE INVENTION

The present invention relates to an arrangement for influencing and/or detecting magnetic particles in a region of action. The present invention relates further to a corresponding method, to a drive field generator unit for such an arrangement and to a computer program.

BACKGROUND OF THE INVENTION

An arrangement of this kind is known from German patent application DE 101 51 778 A1. In the arrangement described in that publication, first of all a magnetic selection field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement has the advantage that it can be used to examine arbitrary examination objects—e.g. human bodies—in a non-destructive manner and without causing any damage and with a high spatial resolution, both close to the surface and remote from the surface of the examination object.

A similar arrangement and method is known from Gleich, B. and Weizenecker, J. (2005), "Tomographic imaging using the nonlinear response of magnetic particles" in nature, vol. 435, pp. 1214-1217. The arrangement and method for magnetic particle imaging (MPI) described in that publication takes advantage of the non-linear magnetization curve of small magnetic particles.

Generally, the drive means of such an MPI arrangement comprises drive field coil units and drive field generator units. For being flexible with the sequences, MPI needs a high reactive power provided by the drive field generator units. Commonly, a switched amplifier is used to generate the high reactive power. This amplifier stores the reactive energy in at the base band (i.e. at zero frequency or a frequency near zero) in a capacitor. To perform this, switching elements have to operate at frequencies in the order of the operation frequency, i.e. at 100 kHz and higher. The switching losses at that frequency are already relatively high. Moreover, the arrangement produces strong high harmonics which implies the use of large filters and even higher reactive power.

WO 2008/078244 A2 discloses an arrangement for influencing and/or detecting magnetic particles, a method for calibrating such an arrangement and a method for influencing and/or detecting magnetic particles in a region of action. The arrangement particularly comprises a compensation controller providing a compensation signal to the drive signal chain and/or to the detection signal chain by means of a coupling means to enhance the signal to noise ratio. One of the signal detection problems occurring in such an arrangement is the induced voltage in the receiving means due to the existence of the magnetic drive field. This induced voltage is typically much larger than the (useful and only interesting) signal voltage of the detection signal. The measurement principle of the arrangement relies on the fact that a magnetic drive field with a dedicated frequency influences the magnetic particles which send out a signal including this frequency but also higher harmonics. These harmonics are measured. Therefore, either the spectrum of the drive field itself must not contain higher harmonics of the dedicated frequency or the higher harmonics of the dedicated frequency have to be eliminated or compensated for—either in the so-called drive signal chain or in the so-called detection signal chain. Especially, it is preferred that the compensation signal is filtered prior to being coupled to the drive signal chain and/or to the detection signal chain. This provides the possibility to add the lowest possible portion of noise to the signals in the drive signal chain and/or the detection signal chain. In this context the term drive signal chain signifies the different stages—e.g. amplifying stage, filtering stage or the like—in order to generate the drive signal fed to the drive means. Likewise in the context of the present invention, the term detection signal chain signifies the different stages—e.g. amplifying stage, filtering stage or the like—in order to generate the detection signal received by the receiving means.

SUMMARY OF THE INVENTION

It is an object of the present invention to provide an arrangement for influencing and/or detecting magnetic particles in a region of action, a corresponding method, a drive field generator unit for such an arrangement and a computer program, by which the number of hardware elements and losses, in particular switching losses in the generation of the required high reactive power.

In a first aspect of the present invention an arrangement is presented that comprises:
  selection means for generating a magnetic selection field having a pattern in space of its magnetic field strength such that a first sub-zone having a low magnetic field strength and a second sub-zone having a higher magnetic field strength are formed in the region of action,
  drive means for changing the position in space of the two sub-zones in the region of action by means of a magnetic drive field so that the magnetization of the magnetic material changes locally, said drive means comprising drive field coil units,
  receiving means for acquiring detection signals, which detection signals depend on the magnetization in the region of action, which magnetization is influenced by the change in the position in space of the first and second sub-zone,
  drive field generator units for generating drive signals for said drive field coil units,
  drive signal amplifiers for amplifying said drive signals,
  coupling means coupled between said drive signal amplifiers and said drive field coil units, said coupling means comprising at least one tank circuit coupled to the output of said drive field amplifiers and a reactive coupling unit coupled between the output of said at least one tank circuit and the input of the respective drive field coil unit, and
  control means for operating said at least one tank circuit at a variable operating frequency.

In a further aspect of the present invention a corresponding method, a drive field generator unit for such an arrangement and a computer program are presented.

Preferred embodiments of the invention are defined in the dependent claims. It shall be understood that the claimed method, the drive means and the computer program have similar and/or identical preferred embodiments as the claimed device and as defined in the dependent claims.

The present invention is based on the idea to store the reactive energy in a tank circuit, which is preferably operating at or near the centre frequency of the MPI drive field (near meaning less than two times outside of the transmission band). Reactive elements, in particular capacitors and/or inductors, couple one or more tank circuit to the drive field resonator. The coupling strength is preferably varied by switching additional reactive elements into and out of the coupling element to vary the strength of coupling.

The switching frequency is preferably in the order of the bandwidth of the drive field system, which is only 1% of the operation frequency which has the advantage that the number of switching events is greatly reduced. A preferred frequency range is from 0 to 5 kHz, in particular from 0 to 2 kHz.

In addition or instead of switching the coupling, the resonance frequency of the energy storage tank circuits can be varied by switched reactive elements. As the frequency of switching is preferably in the order of the drive field bandwidth, it can be synchronised to the MPI sequence to avoid additional noise in the signal and ease the filtering. Thus, the switching can be performed at times where the field free point is moving slowly and no or little signal is generated anyway.

Preferably, said at least one tank circuit preferably comprises switched reactive elements, which are switched at said operating frequency.

In an embodiment said coupling unit comprises two or more reactive coupling elements, in particular inductors and/or capacitors, and switching means for switching at least one of said reactive coupling elements in and out of the signal path to vary the strength of the coupling.

In another embodiment said at least one drive field generator unit comprises at least a second tank circuit coupled in parallel to the first tank circuit. In this way, the reactive energy can be distributed and/or transported between said tank circuits.

Preferably, said control means is adapted for controlling the operating frequency dependent on the changes of the magnetic drive field or of the position in space of the two sub-zones. This control is advantageously adapted such that a switching pulse is generated when the first sub-zone is at or near the edge of the region of action, where the measured detection signal can be neglected anyhow so that any disturbing effects of the switching pulse can be accepted.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
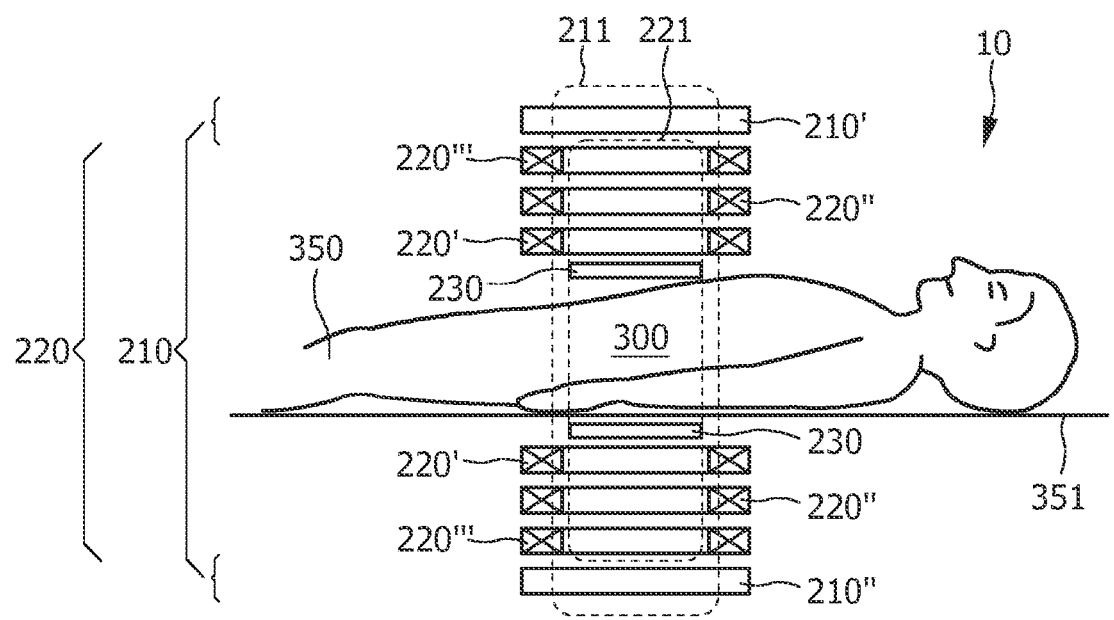
FIG. 1 shows a schematic view of the principle layout of a magnetic particle imaging (MPI) arrangement.

FIG. 1 shows an arbitrary object to be examined by means of a MPI arrangement 10. The reference numeral 350 in FIG. 1 denotes an object, in this case a human or animal patient, who is arranged on a patient table 351, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
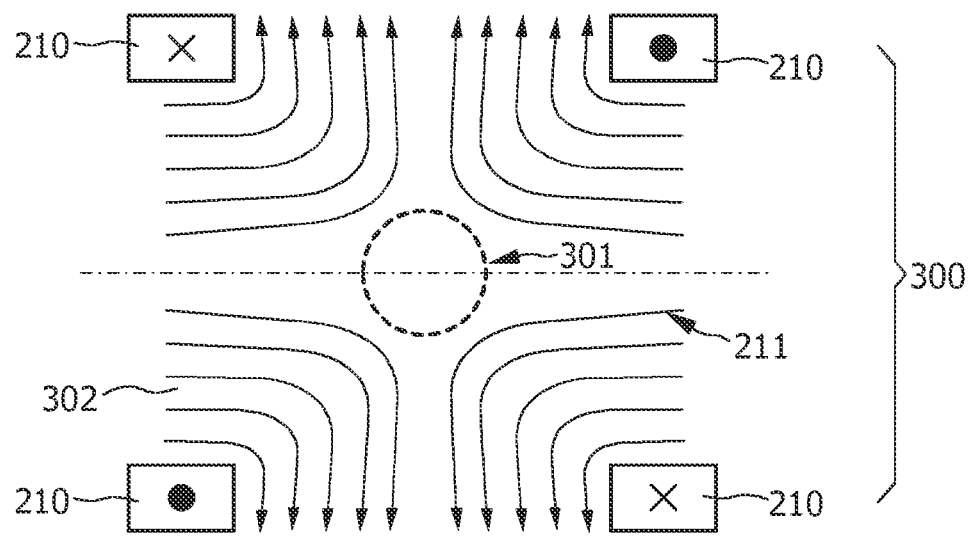
FIG. 2 shows an example of the field line pattern produced by an arrangement according to the present invention.

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameters influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
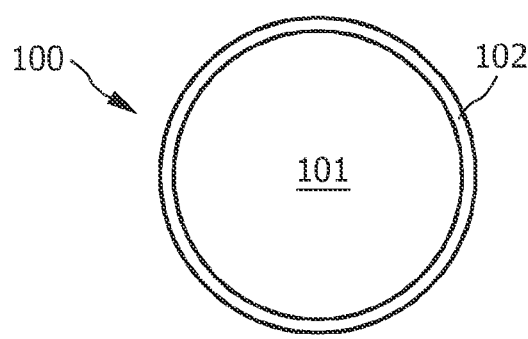
FIG. 3 shows an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 μm, a magnetic field of approximately 800 A/m (corresponding approximately to a flux density of 1 mT) is then required, whereas in the case of a diameter of 100 μm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to $160 \cdot 10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220'' and a fourth coil pair 220''' which together are called drive means 220 in the following. For example, the second coil pair 220' generates a component of the magnetic drive field 221 which extends in the direction of the coil axis of the first coil pair 210', 210'' or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210'', so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220'', 220''' are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220'', 220''' of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220'', 220''' are also arranged above and below the region of action 300 and, therefore, their winding configuration must be different from that of the second coil pair 220'. Coils of this kind, however, are known from the field of magnetic resonance apparatus with open magnets (open MRI) in which a radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210'' as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
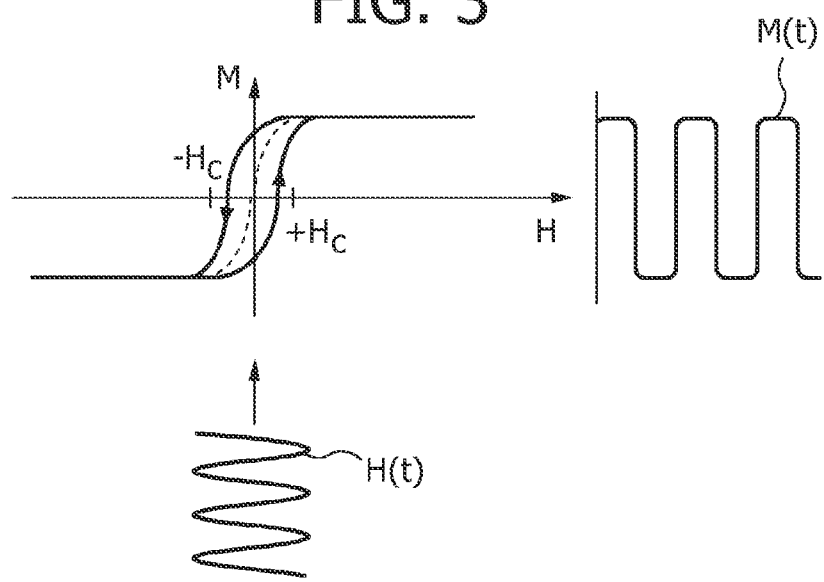
FIGS. 4a and 4b show the magnetization characteristics of such particles.
Figure 4B:
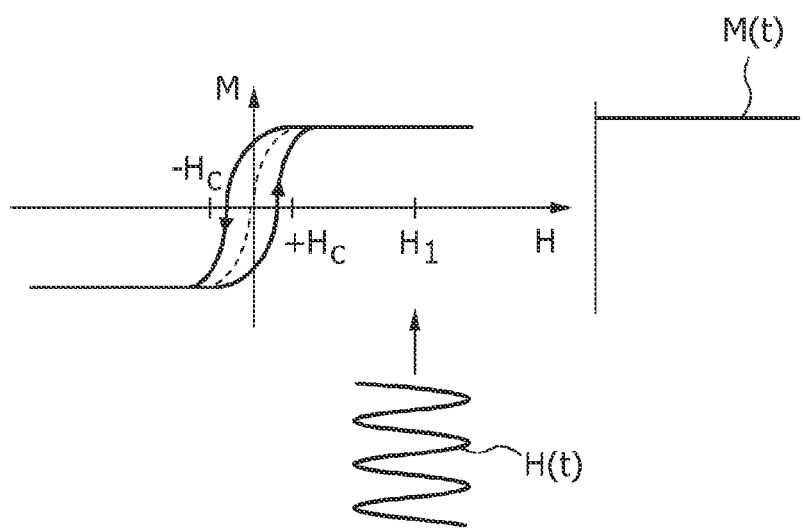

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
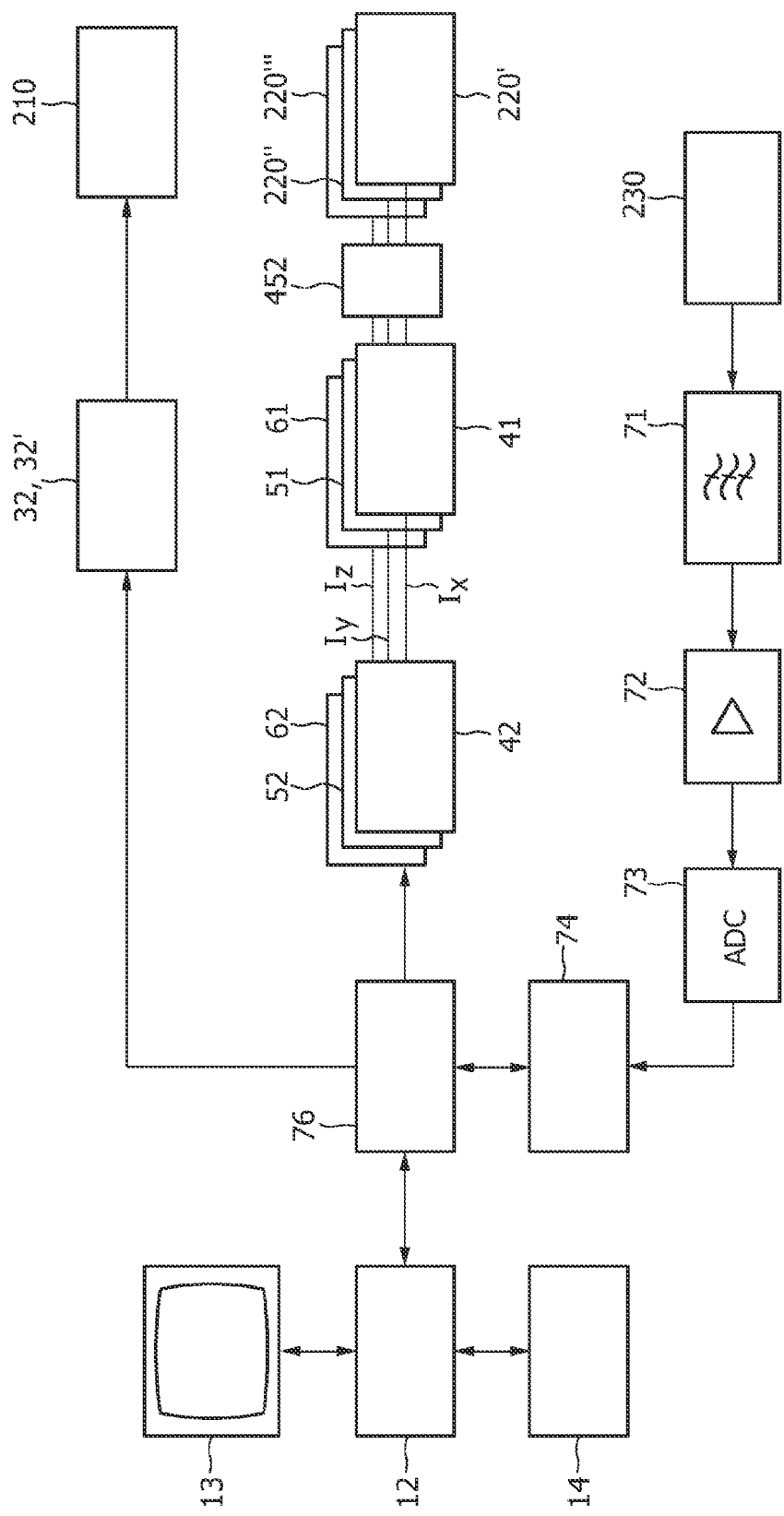
FIG. 5 shows a block diagram of the apparatus according to the present invention.

FIG. 5 shows a block diagram of the apparatus 10 shown in FIG. 1. The selection means 210 is shown schematically in FIG. 5. Preferably, the selection means 210 are provided with three magnetic selection field generation means, in particular coils, permanent magnets or a combination of coils and permanent magnets. Said three magnetic selection field generation means are preferably arranged such that for each spatial direction one magnetic selection field generation means is provided. If in an embodiment coil pairs are provided as magnetic selection field generation means, the coil pairs are supplied with a DC current from a controllable current source 32, said current source 32 being controlled by the control means 76. In order to individually set the gradient strength of the selection field 211 in a desired direction, an overlaid current is overlaid to at least one of coil pairs, wherein the overlaid current of opposed coils is oppositely oriented. In a preferred embodiment, the control means 76 furthermore controls that the sum of the field strength and the sum of the gradient strength of all three spatial fractions of the selection field 211 is maintained at a predefined level.

If in an embodiment permanent magnets are provided as magnetic selection field generation means instead of coil pairs, the current source 32 need to be exchanged by an actuation means 32', e.g. an electro motor, which is able to mechanically move the permanent magnets in order to set the gradient strength in the desired direction according to the control signals provided by the control means 76.

The control means 76 is in turn connected to a computer 12 which is coupled to a monitor 13 for displaying the distribution of magnetic particles in the examination area and an input unit 14, for example a keyboard. A user is therefore able to set the desired direction of the highest resolution and in turn receives the respective image of the region of action on the monitor 13. If the critical direction, in which the highest resolution is needed, deviates from the direction set first by the user, the user can still vary the direction manually in order to produce a further image with an improved imaging resolution. This resolution improvement process can also be operated automatically by the control means 76 and the computer 12. The control means 76 in this embodiment sets the gradient field in a first direction which is automatically estimated or set as start value by the user. The direction of the gradient field is then varied stepwise until the resolution of the thereby received images, which are compared by the computer 12, is maximal, respectively not improved anymore. The most critical direction can therefore be found respectively adapted automatically in order to receive the highest possible resolution.

The coil pairs (second magnetic means) 220', 220", 220' are connected to current amplifiers 41, 51, 61, from which they receive their currents. The current amplifiers 41, 51, 61 are in turn in each case connected to an AC current source 42, 52, 62 which defines the temporal course of the currents Ix, Iy, Iz to be amplified. The AC current sources 42, 52, 62 are controlled by the control means 76.

The receiving coil (receiving means) is also shown schematically in FIG. 5. The signals induced in the receiving coil 230 are fed to a filter unit 71, by means of which the signals are filtered. The aim of this filtering is to separate measured values, which are caused by the magnetization in the examination area which is influenced by the change in position of the two part-regions (301, 302), from other, interfering signals. To this end, the filter unit 71 may be designed for example such that signals which have temporal frequencies that are smaller than the temporal frequencies with which the coil pairs 220', 220", 220'" are operated, or smaller than twice these temporal frequencies, do not pass the filter unit 71. The signals are then transmitted via an amplifier unit 72 to an analog/digital converter 73 (ADC). The digitalized signals produced by the analog/digital converter 73 are fed to an image processing unit (also called reconstruction means) 74, which reconstructs the spatial distribution of the magnetic particles from these signals and the respective position which the first part-region 301 of the first magnetic field in the examination area assumed during receipt of the respective signal and which the image processing unit 74 obtains from the control means 76. The reconstructed spatial distribution of the magnetic particles is finally transmitted via the control means 76 to the computer 12, which displays it on the monitor 13.

For coupling amplified drive signals, generated by said AC current sources 42, 52, 62 and amplified by said current amplifiers (also called drive signal amplifiers) 41, 51, 61, coupling means 452 are coupled between said amplifiers 41, 51, 61 and said coil pairs 220', 220", 220' of said drive means. Details of said coupling means 452 will be explained below in more detail.

Figure 6:
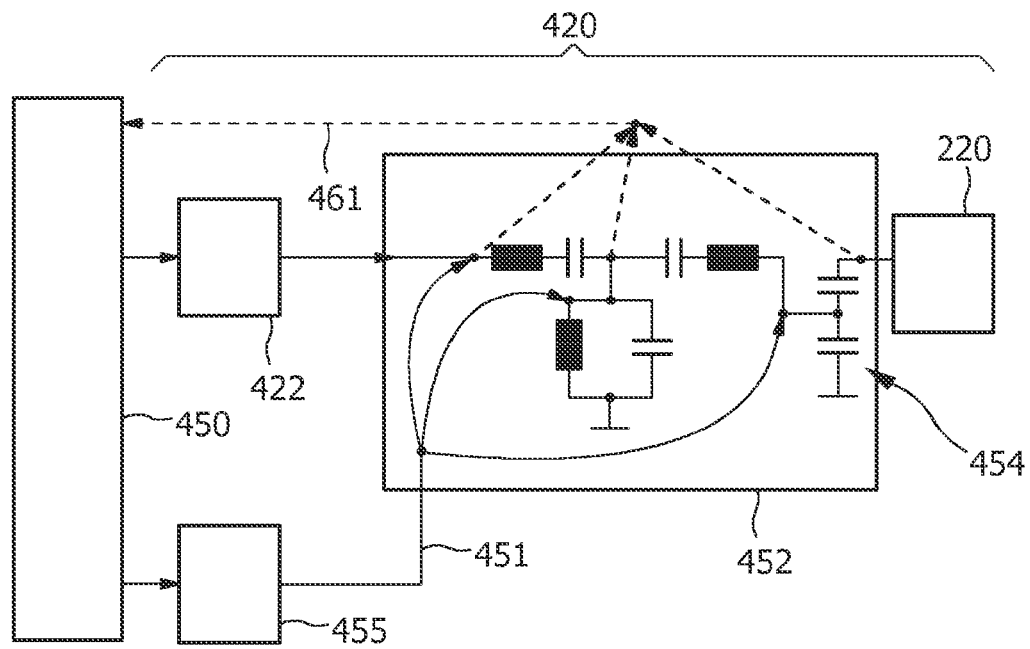
FIG. 6 shows an embodiment of a known coupling unit.

FIG. 6 schematically shows an embodiment of a drive signal chain (for one of the three drive coil pairs 220', 220", 220'") as disclosed in WO 2008/078244 A2. A compensation signal 451 is fed to the drive signal chain 420. A compensation controller 450 generates the drive signal, i.e. the compensation controller 450 comprises the drive signal generator (e.g. 42 in FIG. 5). Especially digital signal generation is realized which allows for more degrees of freedom. The compensation signal 451 is subjected to a broad band signal chain 455 (as a special embodiment of a compensation signal chain). The compensation signal 451 is coupled or fed to the drive signal chain 420 after having passed the broad band signal chain 455. This is done in a way that the higher harmonics in the signal of the drive signal chain 420 are precisely compensated. The feeding or coupling point is preferably not directly after the amplifier stage 422 (comprising the amplifier, e.g. 41, shown in FIG. 5) of the drive signal chain 420 as in that case the needed power for the broad band signal chain 455 would be comparably high.

Different analog filter elements are used at the coupling means 452 as shown in FIG. 6. Especially resistive coupling is used to couple the compensation signal 451 to the drive signal chain 420. Three different coupling points for the compensation signal 451 are shown as alternatives. Preferably, the point of the coupling is chosen such that at least one final passive filter stage 454 is provided after the point of coupling (in the direction towards the drive means 220). This has the advantage that the performance of the arrangement and especially the performance of the compensation is not limited by the precision of the feedback.

Figure 7:
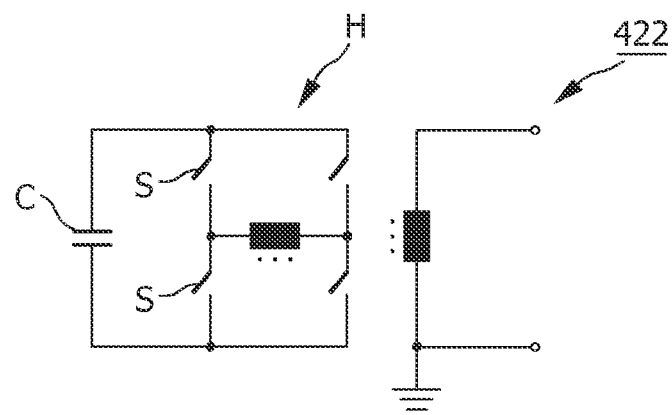
FIG. 7 shows an embodiment of a known amplifier for use with a coupling unit as shown in FIG. 6.

An embodiment of a switched amplifier unit 422 (for one of the drive coil pairs 220', 220'', 220''') commonly used to generate the high reactive power required for MPI is shown in FIG. 7. This amplifier unit 422 stores the reactive energy at the base band in a capacitor C. To perform this, switching elements S, arranged at a H-bridge H, operate at frequencies in the order of the operation frequency, i.e. at 100 kHz and higher. The switching losses at that frequency are already relatively high. Moreover, the amplifier unit 422 produces strong high harmonics which implies the use of large filters and even higher reactive power.

Figure 8:
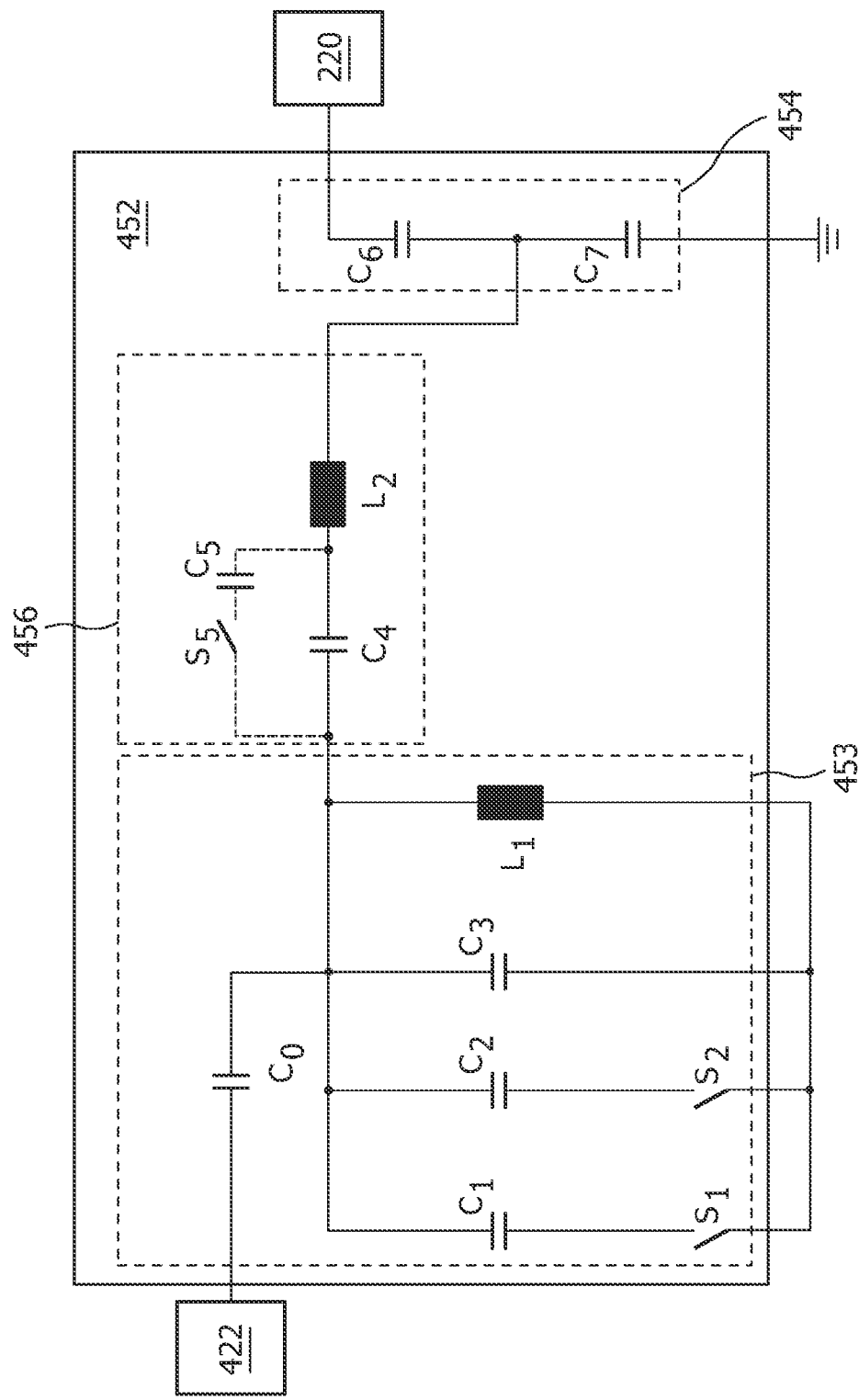
FIG. 8 shows a first embodiment of a coupling unit according to the present invention.

An embodiment of a coupling unit 452 according to the present invention is shown in more detail in FIG. 8. In this figure one coupling unit 452 is shown for one of the three drive field coil pairs 220', 220'', 220''' (here indicated by 220) coupled to the output to one of the amplifiers (41, 51, 61, here indicated by 422). The coupling unit 452 comprises a tank circuit 453 coupled to the output of said drive field amplifier 422, a reactive coupling unit 456 coupled to the output of said tank circuit 453, and a filter unit 454 coupled between the output of said coupling unit 456 and the input of the respective drive field coil unit 220.

The tank circuit 453 comprises a serial capacitor $C_0$ coupled to the output of the amplifier 422. Said serial capacitor $C_0$ is coupled to a tank circuit 456 comprising, in this embodiment, three resonant capacitors $C_1, C_2, C_3$ and a resonant inductor $L_1$, all coupled in parallel, wherein the first and second capacitors $C_1, C_2$ can be uncoupled by switches $S_1, S_2$. Said tank circuit 453 is coupled to a reactive coupling unit 456 comprising a coupling capacitor $C_4$ and a coupling inductor $L_2$, all coupled in series. Optionally, another coupling capacitor $C_5$ is connected in parallel to the coupling capacitor $C_4$, but can be uncoupled by a switch $S_5$. The coupling unit 456 is coupled to the connection point between two filter capacitors $C_6, C_7$ of said filter unit 454.

Thus, according to the present invention, it is proposed to store the reactive energy in the tank circuit 453 operating at or near the centre frequency of the MPI drive field. The reactive elements (capacitors, inductors) of the coupling unit 456 couple said tank circuit 453 to the drive field resonator 454, 220. The coupling strength is varied by switching additional reactive elements, such as the coupling capacitor $C_5$ into and out of the coupling to vary the strength of coupling. The switching frequency is preferably in the order of the bandwidth of the drive field system, which is only 1% of the operation frequency. In this way the number of switching events can be reduced. In addition or instead of switching the coupling, the resonance frequency of the energy storage tank circuit 453 can be varied by switched reactive elements as shown in FIG. 8. As the frequency of switching is in the order of the drive field bandwidth, it can be synchronised to the MPI sequence to avoid additional noise in the signal and ease the filtering. So the switching can be performed at times where the field free point is moving slowly and no signal is generated anyway.

The necessary effective power is provided to the tank circuit 453 by a conventional class AB/H or digital (class D) amplifier 422. According to the present invention the amplifiers needs to deliver only little reactive power, so that it can be relatively small. As the parametric amplifier is inherently a filter, the feeding amplifiers need no extraordinary low distortion.

Switching elements may be MosFETs or bipolar transistors. Diodes or mechanic switches could be also used. If the switching elements operate extremely linear (e.g. no nickel in the leads) they may be used in the drive field resonator if a sequence adapted switching pattern is used. Here, "sequence adapted switching pattern" means (rarely) switching, preferably at turning points of the sequence or points, which have been hit by the FFP already before.

Initially, the system shown in FIG. 8 resonates at a single frequency. To achieve that the amplitude is quickly reduced to zero the coupling factor of the tank circuit 453 with the inductor $L_2$ is reduced by opening the switch $S_5$. Then, the total capacity (formed by the three resonant capacitors $C_1, C_2, C_3$) parallel to resonant inductor $L_1$ is changed such that a phase shift of 180° to the oscillation of the drive coil 220 is achieved. Now, the total capacity (formed by the three resonant capacitors $C_1, C_2, C_3$) parallel to resonant inductor $L_1$ is set to a value, which allows an oscillation with possibly the same frequency as in the drive coil 220. Thus, the coupling is resumed, and energy is able to be transferred from the drive resonance circuit (formed by the filter circuit 454 and the drive coil 220) of the drive coil 220 back to the tank circuit 453. If the oscillation in the drive coil 220 has approximately reached zero amplitude, the coupling will be minimized.

Figure 9:
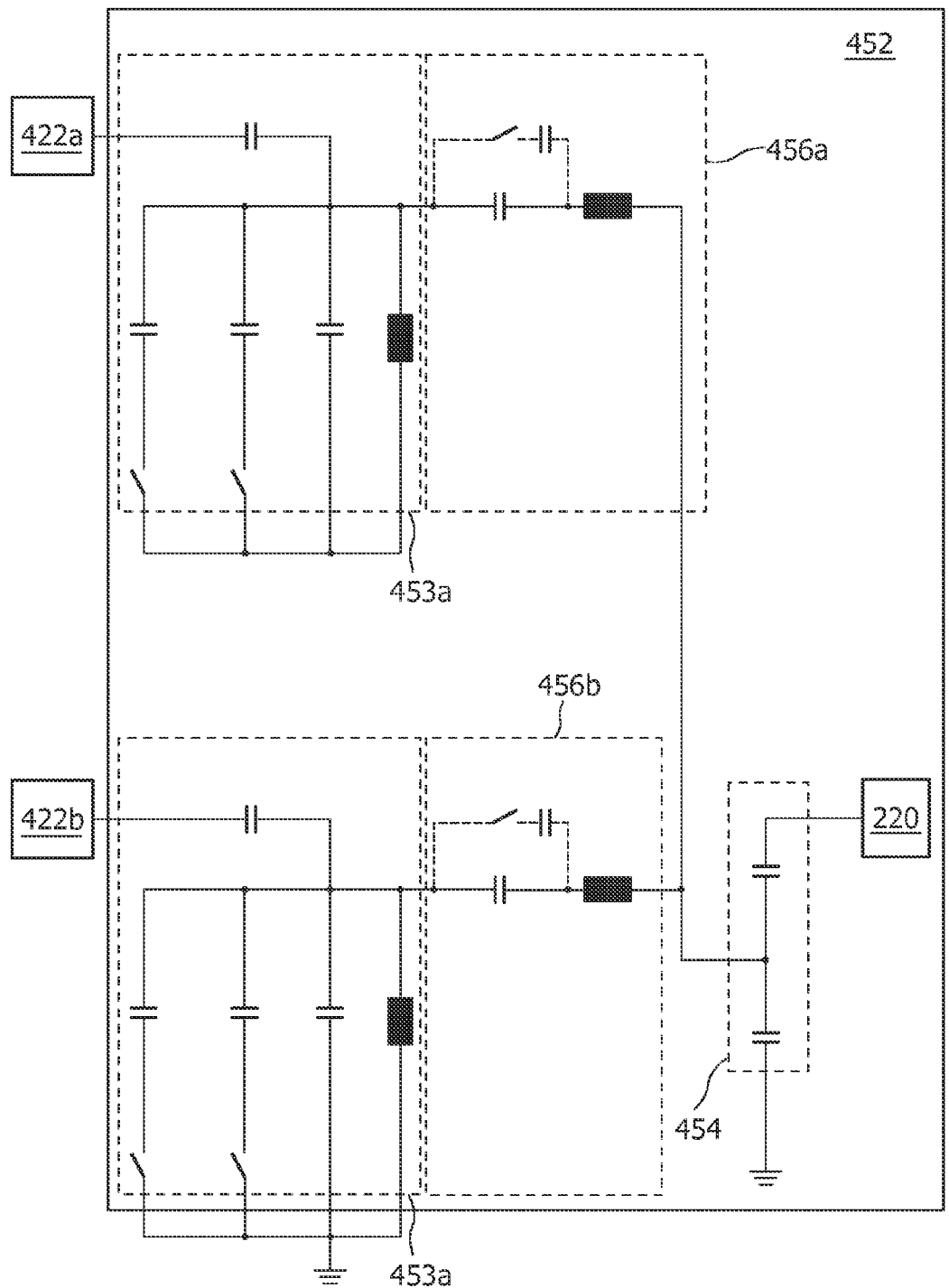
FIG. 9 shows a second embodiment of a coupling unit according to the present invention.

Another embodiment of a coupling unit 452 according to the present invention is shown in FIG. 9. Said embodiment of the coupling unit 452 comprises two tank circuits 453a, 453b (preferably with identical elements as the tank circuit 453 shown in FIG. 8), each coupled to a separate amplifier 422a, 422b (which could also be combined into a common amplifier, or only a single amplifier could be used). The two tank circuits 453a, 453b and the two reactive coupling units 456a, 456b are both coupled to a common filter unit 454. With this embodiment the reactive energy stored in the tank circuits 453a, 453b can be transferred between each other, depending on the switching scheme applied to the switches of the tank circuits 453a, 453b.

With this embodiment a fast start of the oscillation in the drive resonance circuit (formed by the filter circuit 454 and the drive coil 220) can be achieved. Assuming that the two tank circuits 453a, 453b oscillate with the same frequency and amplitude but with a phase shift of 180°, the net current in the drive resonance circuit is zero. Further, it shall be assumed that the amplitude of the oscillation in the drive resonance circuit is also zero. To get the oscillation in the drive resonance circuit quickly started, the capacity in one of the tank circuits 453a, 453b is changed as much as possible, until both tank circuits 453a, 453b oscillation in phase. Then, the capacity is changed back to the original value. Now, that both tank circuits 453a, 453b oscillate in phase, the net current in the drive resonance circuit is maximized, and the drive resonance circuit quickly starts oscillating. It shall be noted that the switch $S_5$ and the coupling capacitor $C_5$ is generally not required for this purpose.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An arrangement for at least one of influencing and detecting magnetic particles in a region of action, wherein the arrangement comprises:
    a selector configured to generate a magnetic selection field having a pattern in space of a magnetic field strength such that a first sub-zone having a low magnetic field strength and a second sub-zone having a higher magnetic field strength are formed in the region of action;
    a driver configured to change a position in space of the two sub-zones in the region of action by a magnetic drive field so that magnetization of the magnetic particles changes locally, said driver comprising drive field coil units; a receiver configured to acquire detection signals, wherein the detection signals depend on the magnetization in the region of action, wherein the magnetization is influenced by a change in the position in space of the two sub-zones, drive field generator units for generating drive signals for said drive field coil units;
    drive signal amplifiers configured to amplify said drive signals;
    a coupler coupled between said drive signal amplifiers and said drive field coil units, said coupler comprising at least one tank circuit coupled to an output of said drive field amplifiers and a reactive coupling unit coupled between an output of said at least one tank circuit and an input of the respective drive field coil unit, wherein said at least one tank circuit comprises a capacitor and an inductor connected in parallel and at least one switched reactive element;
    at least one switch connected in series with the at least one switched reactive element to form a series connection, and configured to connect and disconnect the at least one switched reactive element from the parallel connected capacitor and the inductor, wherein the parallel connected capacitor and inductor are further connected in parallel with the series connection of the at least one switch and the at leapt one switched reactive element; and
    a controller configured to operate said at least one tank circuit at a variable operating frequency by opening and closing the at least one switch to connect and disconnect the at least one switched reactive element from the parallel connected capacitor and the inductor.

2. The arrangement as claimed n claim 1,
    wherein said variable operating frequency is an order of a bandwidth of the magnetic drive field.

3. The arrangement as claimed in claim 1,
    wherein said variable operating frequency is in a frequency range from 0 to 5 kHz.

4. The arrangement as claimed in claim 1,
    wherein said coupler comprises two or more reactive coupling elements and switches configured to switch at least one of said two or more reactive coupling element in and out of a signal path to vary a strength of the coupling.

5. The arrangement as claimed in claim 1,
    wherein said at least one tank circuit of said coupler comprises a first tank circuit and a second tank circuit coupled in parallel to the first tank circuit.

6. The arrangement as claimed in claim 1,
    wherein said controller is further configured to control the variable operating frequency dependent on changes of the magnetic drive field or of the position in space of the two sub-zones.

7. The arrangement as claimed in claim 6,
    wherein said controller is further configured to control the variable operating frequency such that a switching pulse is generated when the first sub-zone is at or near an edge of the region of action.

8. The arrangement of claim 1, wherein said variable operating frequency is in a frequency range from 0 to 2 kHz.

9. A method for influencing and/or detecting magnetic particles in a region of action, wherein the method comprises the acts of:
    generating a magnetic selection field having a pattern in space of a magnetic field strength such that a first sub-zone having a low magnetic field strength and a second sub-zone having a higher magnetic field strength are formed in the region of action;
    changing a position space of the two sub-zones in the region of action by a driver configured to generate a magnetic drive field as that a magnetization of the magnetic particles changes locally, said driver comprising drive field coil units;
    acquiring detection signals, wherein the detection signals depend on the magnetization in the region of action, wherein the magnetization is influenced by a change in the position in space of the two sub-zones;
    generating drive signals for said drive field coil units;
    amplifying said drive signals;
    coupling said amplified drive signals to said drive field coil units by a coupler comprising at least one tank circuit coupled to an output of said drive field amplifiers and a reactive coupling unit coupled between an output of said at least one tank circuit and an input of a respective drive field coil unit, wherein said at least one tank circuit comprises a capacitor and an inductor connected in parallel and at least one switched reactive element; and
    operating said at least one tank circuit at a variable operating frequency by opening and closing at least one switch connected in series with the at least one switched reactive element to form a series connection, and to connect and disconnect the at least one switched reactive element from the parallel connected capacitor and the inductor, wherein the parallel connected capacitor and inductor are further connected in parallel with the series connection of the at least one switch and the at least one switched reactive element.

10. A non-transitory computer readable medium comprising computer instructions which, when executed by a processor, configure the processor to perform the acts of:

generating a magnetic selection field having a pattern in space of a magnetic field strength such that a first sub-zone having a low magnetic field strength and a second sub-zone having a higher magnetic field strength are formed in a region of action;

changing a position in space of the two sub-zones in the region of action by a driver configured to generate a magnetic drive field so that a magnetization of the magnetic particles changes locally, said driver comprising drive field coil units;

acquiring detection signals, wherein the detection signals depend on the magnetization in the region of action, wherein the magnetization is influenced by a change in the position in space of the two sub-zones;

generating drive signals for said drive field coil units;

amplifying said drive signals;

coupling said amplified drive signals to said drive field coil units by coupler comprising at least one tank circuit coupled to an output of said drive field amplifiers and a reactive coupling unit coupled between an output of said at least one tank circuit and an input of a respective drive field coil unit, wherein said at least one tank circuit comprises a capacitor and an inductor connected in parallel and at least one switched reactive element; and operating said at least one tank circuit at a variable operating frequency by opening and closing at least one switch connected in series with the at least one switched reactive element to form a series connection, and to connect and disconnect the at least one switched reactive element from the parallel connected capacitor and the inductor, wherein the parallel connected capacitor and inductor are further connected in parallel with the series connection of the at least one switch and the at least one switched reactive element.

* * * * *